United States Patent
Belz

(10) Patent No.: US 8,189,196 B2
(45) Date of Patent: May 29, 2012

(54) SELF REFERENCING LED DETECTION SYSTEM FOR SPECTROSCOPY APPLICATIONS

(75) Inventor: Mathias Belz, Sarasota, FL (US)

(73) Assignee: World Precision Instruments, Inc., Sarasota, FL (US)

( * ) Notice: Subject to any disclaimer, the term of this patent is extended or adjusted under 35 U.S.C. 154(b) by 0 days.

(21) Appl. No.: 13/082,087

(22) Filed: Apr. 7, 2011

(65) Prior Publication Data
US 2011/0188042 A1    Aug. 4, 2011

Related U.S. Application Data

(63) Continuation of application No. 12/009,492, filed on Jan. 18, 2008, now abandoned.

(60) Provisional application No. 60/885,888, filed on Jan. 20, 2007.

(51) Int. Cl.
*G01N 21/25* (2006.01)
(52) U.S. Cl. .................................................. 356/420
(58) Field of Classification Search .................. 356/420
See application file for complete search history.

(56) References Cited

U.S. PATENT DOCUMENTS

| 2003/0116436 A1* | 6/2003 | Amirkhanian et al. ........ 204/452 |
| 2005/0285129 A1* | 12/2005 | Jackson et al. ................. 257/98 |

* cited by examiner

*Primary Examiner* — Tarifur Chowdhury
*Assistant Examiner* — Abdullahi Nur
(74) *Attorney, Agent, or Firm* — Alix, Yale & Ristas, LLP

(57) ABSTRACT

A light emitting diode (LED) based detection system is employed for spectroscopy based applications. LEDs are used as monochromatic light sources for applications at specific and pre-defined wavelengths. Spectrographic information is generated using LEDs of different wavelengths ranging from 260 nm to 1400 nm. Multiple wavelength information is generated by coupling light from each LED into an intensity and mode mixing fiber bundle. A dual beam approach of using a reference and a sample photodiode ensures automatic drift correction. Interference filters at the LED input fiber reduce the spectral bandwidth of the monochromatic light emission to a useful 10 nm bandwidth by cutting off the LEDs trailing emission distribution allowing for absorbance measurements similar to typical spectrometers.

20 Claims, 8 Drawing Sheets

US 8,189,196 B2

SELF REFERENCING LED DETECTION SYSTEM FOR SPECTROSCOPY APPLICATIONS

CROSS-REFERENCE TO RELATED APPLICATION

This application is a continuation of U.S. patent application Ser. No. 12/009,492 filed Jan. 18, 2008, which claims the priority of U.S. Provisional Application No. 60/885,888 filed Jan. 20, 2007, the entire contents of which are incorporated herein.

BACKGROUND

Absorption spectroscopy uses the range of electromagnetic spectra in which a substance absorbs. In absorption spectroscopy light of a particular wavelength is passed through the sample. After calibration, the amount of absorption can be related to the sample concentration through the Beer-Lambert law. Examples of absorption spectroscopy include, for example, ultraviolet/visible (UV/VIS) absorption spectroscopy (most often performed on liquid samples to detect molecular content) and infrared (IR) spectroscopy (most often performed on liquid, semi-liquid (paste or grease), dried, or solid samples to determine molecular information, including structural information).

Spectroscopic analysis typically uses a spectrometer. The spectrometer typically includes a radiation source such as a deuterium, tungsten or xenon lamp capable of emitting radiation over a very broad range of wavelengths. The light is coupled into a sample held in a sample cell. The spectrometer filters the light emitted by the lamp, before or after coupling with the sample, by use of monochromators, filters, gratings, etc. A detector, for example, a photodiode, photomultiplier, photodiode array, or CCD array, quantifies the amount of light passed through (absorption) or emitted by (fluorescence) the sample to provide a detectable signal. While this equipment provides analysis flexibility, it also requires complicated and expensive light sources, gratings, monochromators and other components to take advantage of this flexibility.

Some experiments and tests do not need a spectrometer with full wavelength coverage, but may be performed using light in a single wavelength or only a few wavelengths. For example, applications in the oceanographic field include nutrient analysis, e.g. nitrite/nitrate requiring light at only 540 nm, phosphate requiring light at only 880 nm or 710 nm and iron requiring light at only 562 nm when using colorimetric techniques. Further, applications in biochemistry include protein detection, which could either be performed directly in the UV at 280 nm, or via colorimetric techniques, such as the modified Lowry Protein Assay, with detection at 650 nm (normalized at 405 nm) or the Bradford Assay, where the bound protein-dye complex is measured at 595 nm and can be normalized in the 700 to 750 nm region. Most of these analyses can be performed using single wavelength detection. Their accuracy could be improved by using a second wavelength for baseline offset and a third and/or fourth wavelength for simple absorbance shape detection to eliminate or indicate other colorimetric substances in the sample solution and correct for them. However, in some applications these improvements are not needed.

LEDs have long been used as quasi-monochromatic light sources. They are readily available for nearly all parts of visible light spectra. Recently UV LEDs with emission wavelength as low as 250 nm have become commercially available. Belz, M., *Photonics West* 2007. Many application specific LED-based detection systems have been developed and patented. Recently, an optical arrangement for assay strips was designed and disclosed in U.S. Pat. No. 7,315,378. It purportedly allowed the reliable reading of optical test strips and was based on several LEDs and photodetectors. These detection systems usually rely on single wavelength detection and may use a second photodiode to correct for the inherent drift behavior of the LED. A filterless chromatically variable light source, wherein light is coupled via optical fibers from several LEDs into a single optical fiber is disclosed in U.S. Pat. No. 5,636,303. The disclosed light source allowed individual control of the intensity of each LED to generate either light of a particular wavelength or a white light spectrum.

SUMMARY OF THE DISCLOSURE

A self-referencing LED based detection system with multiple wavelengths (LEDs) is employed for spectroscopy applications. The system may be exemplified by a flow injection based absorbance detection system, but is not limited to this application and may be used for small sample volume discrete measurements, as well as for fluorescence applications. Although LEDs have the tendency to drift in light output power as a function a temperature caused by self-heating, stable output powers can be achieved by driving them in constant current mode and measuring their output with a reference detector. Detection at multiple wavelengths is realized by using several LEDs which emit at different wavelengths, coupling each of them into an optical fiber and coupling these fibers into a single fiber of large diameter for mixing their emission spectra and providing a stable consistent light output at the end of the large mixing fiber. Light is coupled to a reference photodiode and to the fiber optic output at the end of the fiber.

A sample cell is connected to the detection system via the fiber optic output and the sample photodiode input. LEDs are switched on and off sequentially. Light output is measured simultaneously by the reference photodiode and the sample photodiode. Thus, dark, reference and sample intensity are detected simultaneously and any LED drift or stray light can be corrected for automatically, ensuring precise measurements and long-term drift stability. To reduce the spectral bandwidth of the LEDs, interference filters are either placed between the LED and the coupling fiber or are coated directly on the LED coupling fiber to optimize light throughput.

DETAILED DESCRIPTION OF THE PREFERRED EMBODIMENTS

An LED based spectrophotometric detection system performs absorbance or fluorescence spectroscopy and may take several forms as described below. One LED provides light at one wavelength or by manually or automatically sequentially switching LEDs of different colors (wavelengths) tailored for specific applications. In advantageous variations the detection system may use a standard interface such that different LED emission modules, each with LEDs selected for a specific wavelength, can be attached. Advantageously, the LED or LED modules selected will each provide light in a narrow wavelength range falling within the UV, VIS, NIR and IR region of the light spectrum. Such LEDs or LED emission modules are supplied with power to emit light. The emitted light is coupled into a sample held in a fiber optic sample cell, such as a flow cell, long path cell, dipping probe, external curette holder or a reflection probe. In one embodiment the sample is contained in a liquid wavelength capillary cell (LWCC) marketed by World Precision Instruments, Inc. Other compatible commercial sample cells are fiber optic curette holders, DipTip™ fiber optic probes and SpectroPipetter™ probes marketed by World Precision Instruments, Inc.

A detector measures light passed through (absorption) or emitted by (fluorescence) the sample to provide an indication of the presence and/or amount of the sample present. An LED based detection system used to measure fluorescence signals would have much higher sensitivity than standard fiber optic based spectrometers. A commercially available low noise photodiode is used to detect LED emissions.

Figure 1:
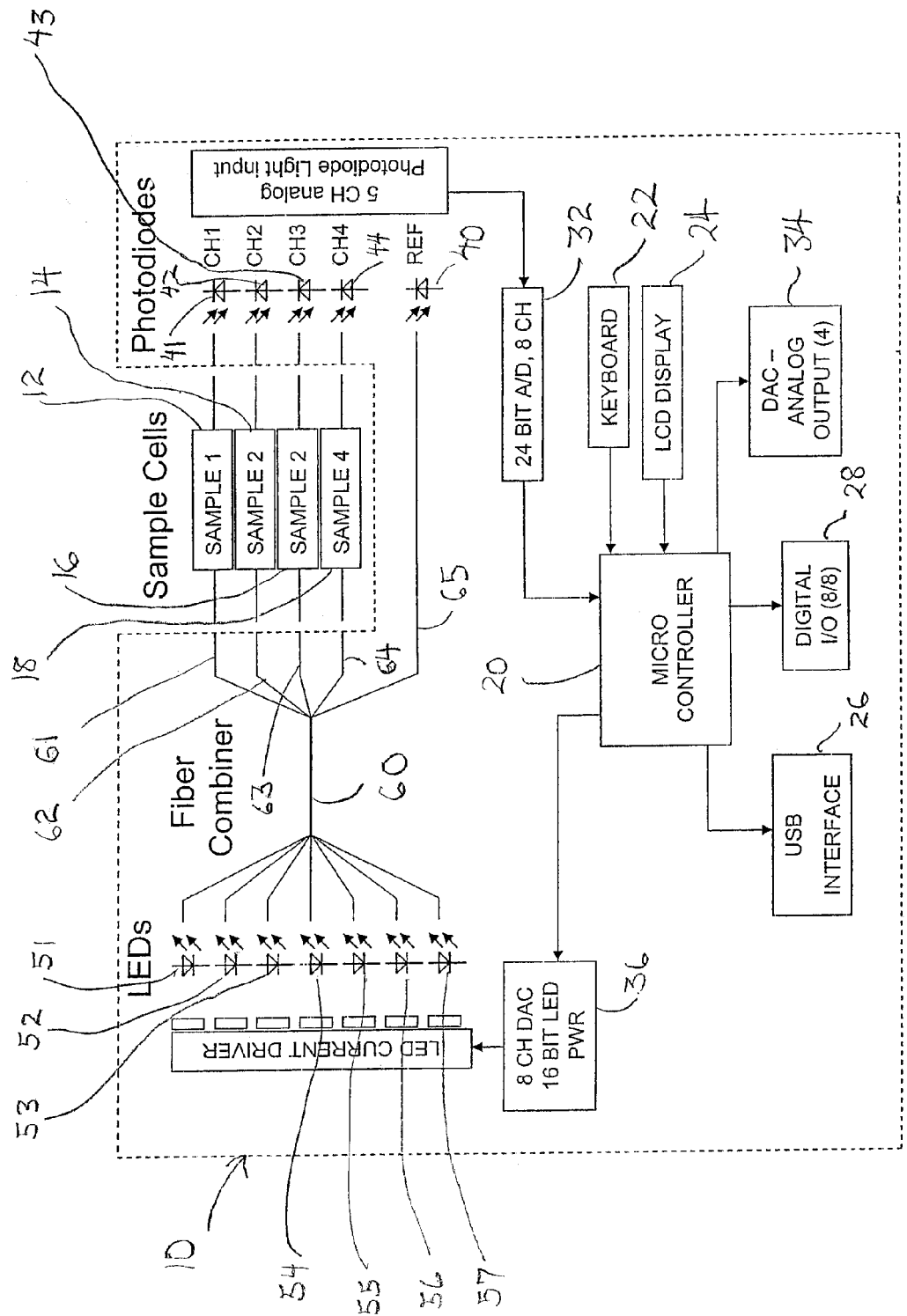
FIG. 1 is an annotated block diagram of an LED detection instrument and associated sample cells.

With reference to FIG. 1 a colorimetric detection instrument designated generally by the numeral 10 is illustrated as it interfaces with four sample cells 12, 14, 16 and 18 containing samples 51, 52, 53 and 54 respectively. Advantageously, the instrument 10 provided by the system functions like a dual beam spectrometer for specific wavelength applications. In this embodiment, as described below the instrument 10 is self correcting for LED intensity drift by use of a reference channel, self correcting for ambient light by measurement of dark current after each pulsed sample or reference measurement and has the capability to work with a phase locked loop to reject AC type stray light influencing the light measurement.

Figure 2:
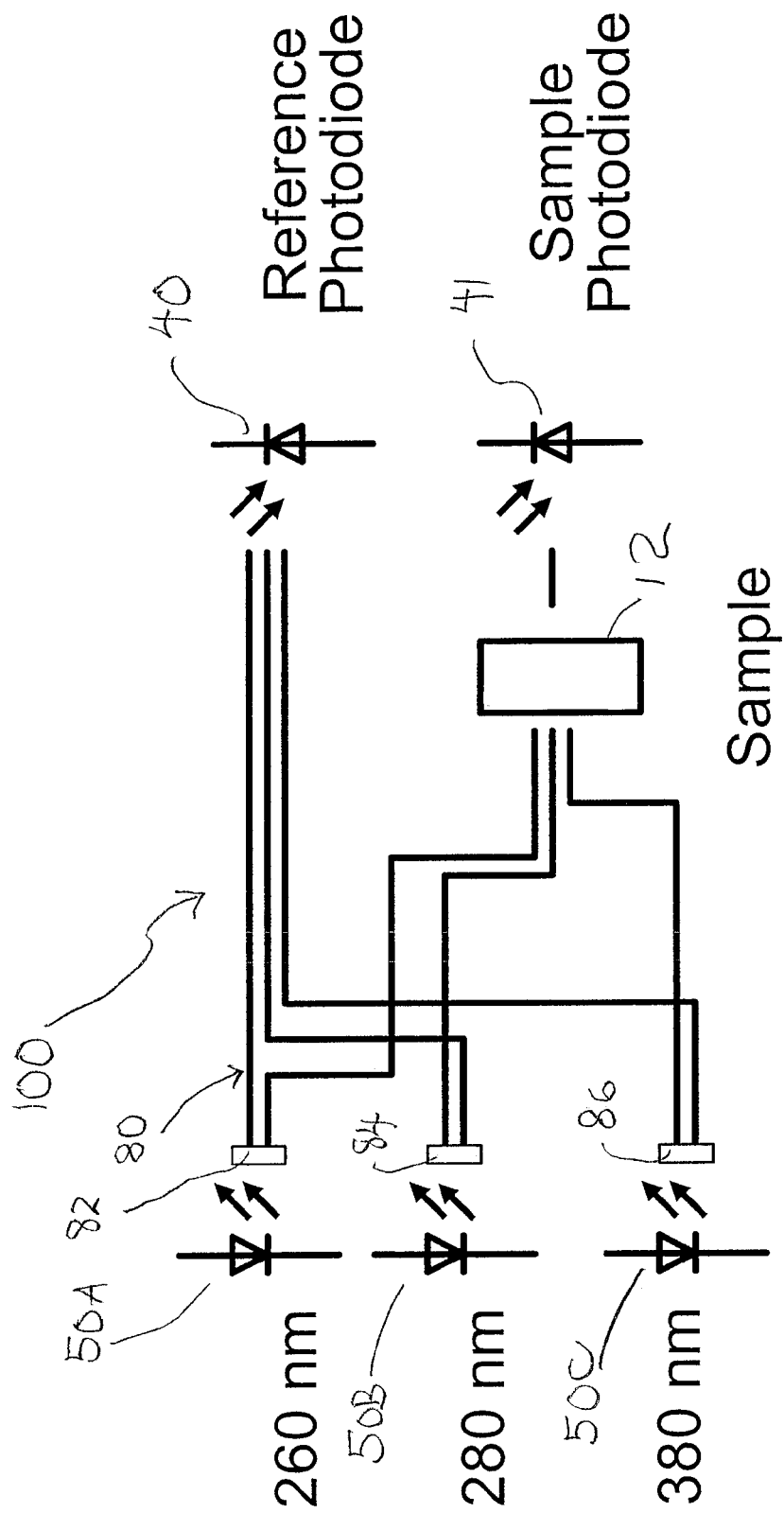
FIG. 2 is an annotated block diagram of a UV LED detection system with a reference channel for biochemistry applications.
Figure 3:
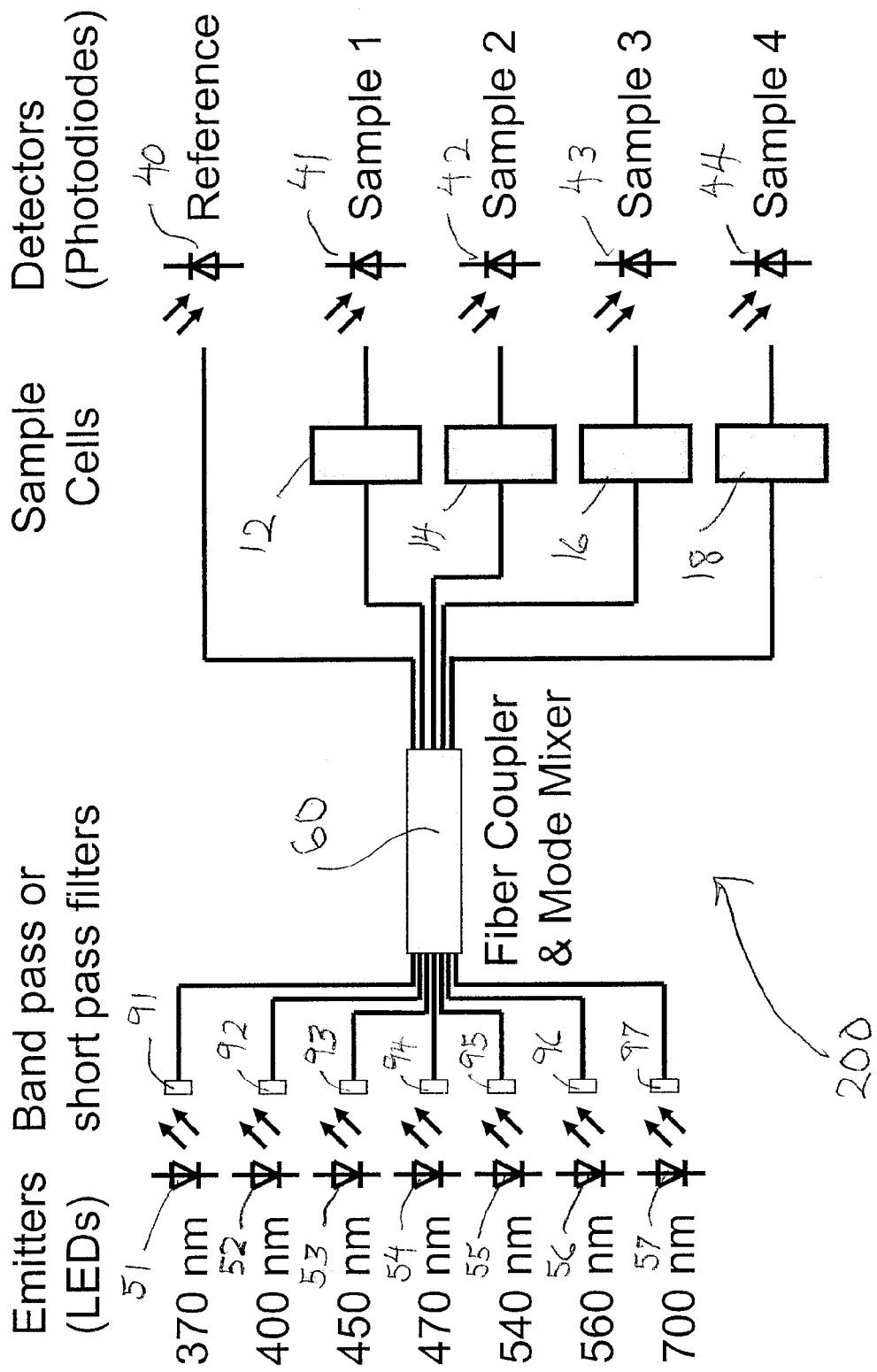
FIG. 3 is an annotated block diagram of multi-channel VIS LED detection system with a reference channel for oceanographic and process control applications.

With additional reference to FIGS. 2 and 3, embodiments of additional LED detection systems 100 and 200 adapted for specific applications are schematically illustrated. Block functions, inputs and outputs for the various embodiments are discussed with reference to FIG. 1. The instrument has a mechanical interface that will accept two or more LEDs or LED modules of different wavelengths which are selected for a specific analysis to be undertaken. A microcontroller 20 provides control and interface signals to the system components. The microcontroller 20 provides timing and on/off control for the LED drivers 30.

A detector, for example a photodiode, is used to detect light passed through, or emitted by, the samples and, advantageously, from the reference. The detector current is converted to voltage. This analog voltage may then advantageously be converted into a digital signal by ND 32 that will be sent to the microcontroller 20. Reference and post experiment scaled and converted data may be provided as inputs from the A/D converter 32. The post experiment data will be sent as an output to the digital to analog converter (DAC) 34 to provide analog values. The instrument has a mechanical interface that will accept two or more LEDs or LED modules of different wavelengths which are selected for a specific analysis to be undertaken.

Detection instrument 10 functions as a self-referencing optical detection system. Light Emitting Diodes (LEDS) 51-57 are used as quasi-monochromatic light sources. They are sequentially switched on and off to generate a train of light intensities at different wavelengths. Up to 7 LEDS are possible in this arrangement. In this arrangement, light of the different LEDs is coupled via a optical fiber of e.g. 750 μm/m core diameter into a 3000 μm/m "fiber combiner" 60. The fiber combiner 60, uniformly combines and mixes the light. Light is coupled out of the combiner into five separate output fibers 61-65. One fiber 61 is directly connected into a reference photodiode 40. The purpose of the reference diode 40 is to quantify the LED light output and use it to compensate for light power drift of the LED during the measurement cycle.

A 16 bit digital to analog converter (DAC) 36 is used to control the output of each individual LED 51-57, matching it to the samples S1, S2, S3, S4, used. Four optical fibers 61-64 are used to provide light to four independent external sample cells 12, 14, 16, 18 (Sample 1, 2, 3 & 4). Light is coupled into and out of the sample cells via optical fibers. Four separate photodiodes 41-44 are used to measure the corresponding light levels exiting the sample cells. A 24 bit A/D converter 32 is used to convert the analog signals from the photodiodes 40-44 into the digital domain.

Figure 4:
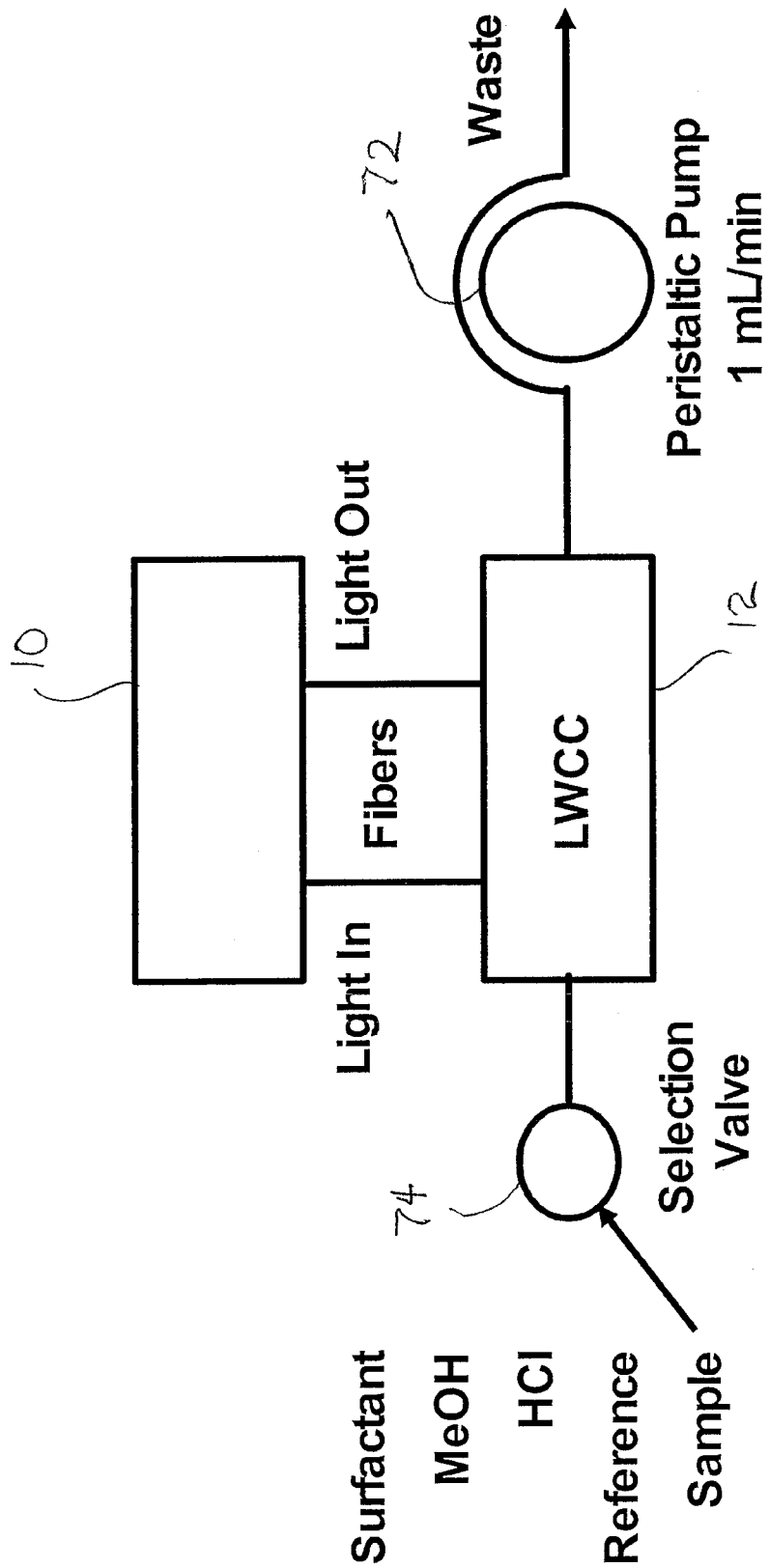
FIG. 4 is an annotated block diagram of a single channel setup of a flow injection system.

The microcontroller 20 is used to control all aspects of the measurement cycle. The 8 channel DAC 36 controlling the LED power allows the instrument to optimize light throughput in the sample cells, tailoring the light output of the sample cells to the analog photodiode input of the instrument. A simple keyboard 22 allows for setting the parameters of a measurement cycle. Parameters and measurement results are displayed on the LCD display 24. The measurement result is scaled to the DAC-Analog Output 34 and is further available in digital format via the USB interface 26. Eight digital inputs and eight outputs 28 are available to receive trigger inputs and run experimental setups, such as, for example, pump 72 and valve 74 illustrated in FIG. 4.

Methods can be programmed to automate experimental procedures, such as e.g. fluid injection based nitrite/nitrate or phosphate analysis. Further, a software package can communicate via the USB interface 26 with the detection instrument to change parameters and receive and store experimental data. In a single measurement cycle, dark readings, sample readings and reference readings are collected. One advantage of the system is that due to its monochromatic light excitation principle, stray light effects are far smaller than in traditional spectrometer systems. Thus, the upper limit of the dynamic range of the detection system is increased from the traditional 2 AU to 3-4 AU. A second advantage of the system is that due to the constant tracking of the reference signal, signal drift is virtually non-existent. Absorbance drifts smaller than 0.5 mAU over a period of several days have been obtained. Thirdly, due to the constant detection of the dark output, stray light induced offsets from external light collection are automatically corrected for. Fourthly, synchronous detection of sample and reference signals is possible.

The following examples are included for purposes of illustration so that the disclosure may be more readily understood and are in no way intended to limit the scope of the disclosure unless otherwise specifically indicated.

DNA and RNA Detection Example

With reference to FIG. 2, LED detection system 100 which shows how detection instrument 10 may be configured for DNA and RNA detection, employs three UV LEDs (260, 280, 380 nm) designated 50A, 50B and 50C. Fiber optic coupling connects the LEDs to the reference photodiode 40 and the sample photodiode 41 via a sample cell 12. LEDs 50A, 50B, 50C were driven in current mode with 10 to 20 mA. A fiber optic bundle 80 with three input (one per LED) and two outputs for the reference and the sample channel was prepared from solarization resistant fused silica fibers. A fiber optic cuvette holder and standard 10 mm quartz cuvettes were used for sample analysis.

Traditional LEDs have a spectral bandwidth in the area of 7-30 nm with a trailing edge towards the longer wavelength. A typical biochemistry example is the detection of DNA and BSA concentrations at 260 nm and 280 nm, respectively. Pure DNA exhibits an absorbance of 1.0 AU at 260 nm for a 50 µg/mL concentration, whereby a BSA standard solution of 2.0 mg/mL has an absorbance of 1.33 AU at 280 nm. Further, the purity of DNA can be determined calculating the absorbance ratio at 260 nm and 280 nm, which should be 1.8 or above. However, to perform the measurements correctly, the spectral instrument bandwidth has to be accounted for. The spectral measured bandwidth full bandwidth half maximum (FWHM), of the clearly defined DNA and BSA absorbance peak is approximately 43 nm and 31 nm, respectively. Traditionally, measurements are performed with detector systems having a spectral bandwidth (FWHM) of $\frac{1}{10}^{th}$ of the sample absorbance peak. This would result in an instrument bandwidth requirement of 4.3 nm and 3.1 nm for BSA and DNA. Nevertheless, in recent years, spectrophotometers with bandwidth of 5 nm and above have been used routinely in life science research for quantification and purity determination of DNA. In a first approximation, the spectral bandwidth of DNA and BSA can be estimated to 43 nm and 31 nm, respectively. The peaks are spaced 20 nm apart, but overlap significantly. DNA purity can be assessed by calculating the absorbance ratio at 260 nm and 280 nm. Pure DNA, as used in this example exhibits an absorbance ratio A260/A280>1.8

Following the Beer-Lambert-Bouguer law, the spectral absorbance, $ABS_{Sample-Spec}(\lambda)$, through a sample, is as follows:

$$ABS_{Sample-Spec}(\lambda) = \frac{I_{Ref}(\lambda)}{I_{Sam}(\lambda)} = \varepsilon(\lambda)lc. \quad (1)$$

It is proportional to the sample concentration, c, the path length, l, and its material specific extinction coefficient, $\varepsilon(\lambda)$, where $I_{Ref}(\lambda)$ is the incident or reference intensity, $I_{Sam}(\lambda)$ is the transmitted or sample intensity and $\lambda$ is the wavelength of light. The spectral (reference) intensity distribution of a LED, $I_{REF-LED}(\lambda)$, can be approximated by a Gaussian intensity distribution as follows:

$$I_{Ref-LED}(\lambda) = I_0 10^{\frac{ln(2)(\lambda-\lambda_c)^2}{(\frac{FWHM}{2})^2}}. \quad (2)$$

where $I_0$ is the peak intensity, $\lambda_c$ is the center wavelength of the LED or filter, if used, and FWHM represents the spectral bandwidth measured as Full Width Half Maximum. Thus, the LED light intensity distribution transmitted through the sample, $I_{Sam-LED(\lambda)}$ may be written as:

$$I_{Sam-LED}(\lambda) = I_{Ref-LED}(\lambda) 10^{-ABS_{Sample-Spec}(\lambda)} \quad (3)$$

However, in the optical setup used, light intensity is detected by a photodiode; in this case, the total absorbance of the sample, $ABS_{Sample-LED}$, measured with the LED detection scheme can be estimated to be:

$$ABS_{Sample-LED} = \log \int_{\lambda_1}^{\lambda_2} \frac{I_{Ref-LED}(\lambda)}{I_{Sam-LED}(\lambda)} d\lambda \quad (4)$$

where $\lambda_1$ and $\lambda_2$ are the lower and the upper limit, defined by a reduction of spectral intensity to less than 5% related to the maximum 100% at center peak wavelength.

Figure 6:
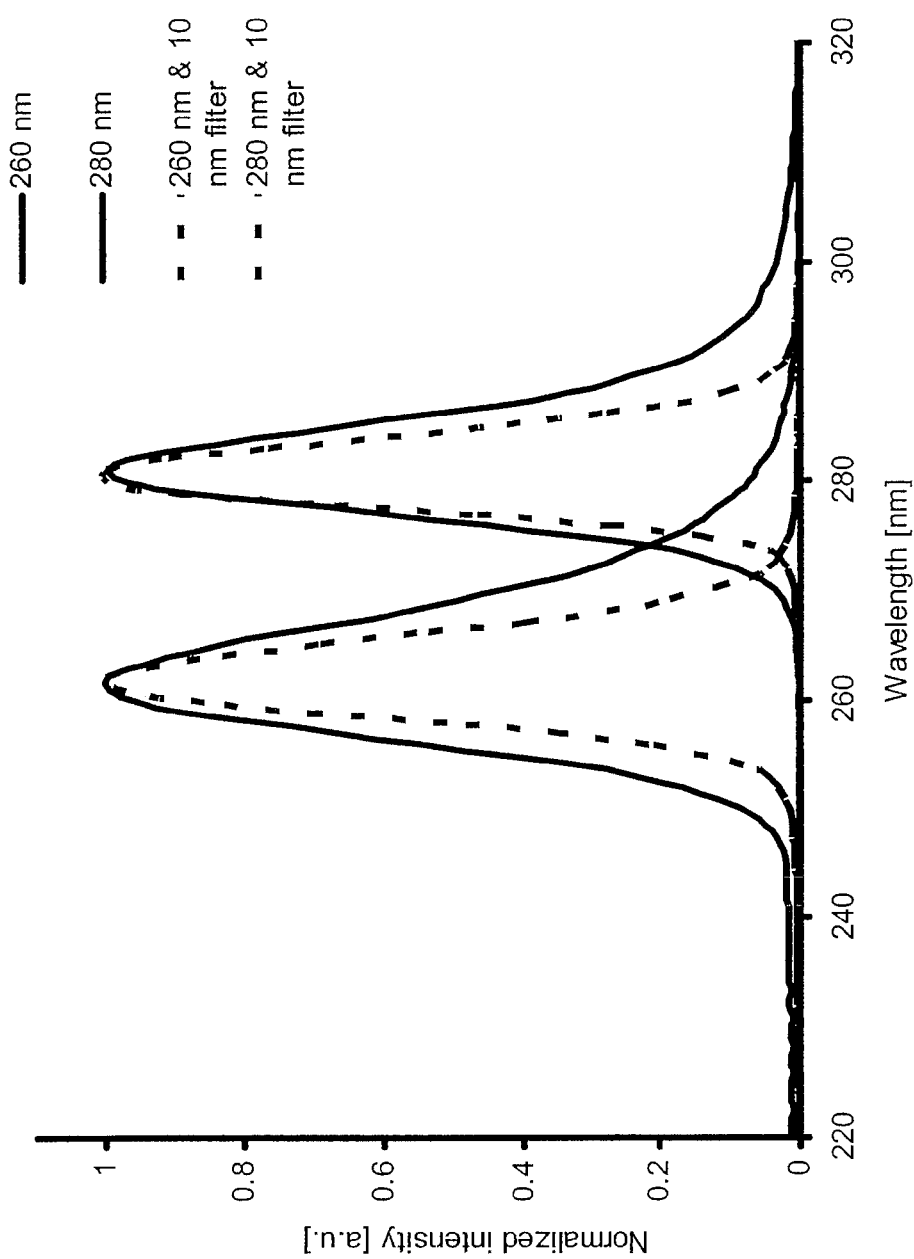
FIG. 6 is a graph of a normalized intensity distribution of UV LEDs with a center wavelength of 260 nm and 280 nm, with and without a 10 nm interference filter.
Figure 7:
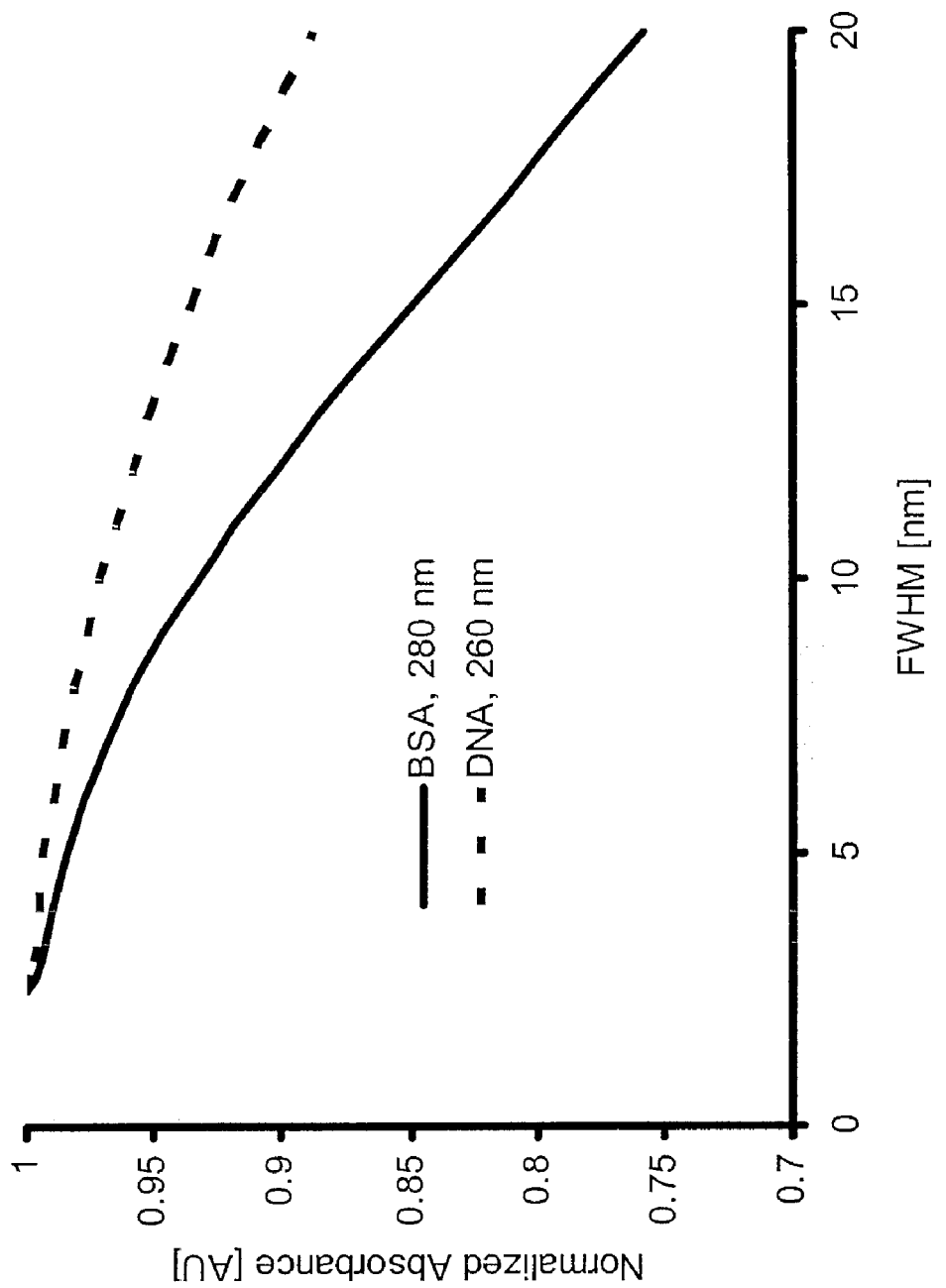
FIG. 7 is a graph of a simulated decrease of absorbance for DNA at 260 nm and BSA at 280 nm wavelength as a function of increasing the spectral bandwidth (FWHM) of a detection system.

The effect of increasing the spectral bandwidth, measured as FWHM, of the detection system on the absorbance signal, when measuring DNA and 260 nm and BSA at 280 nm was simulated using equations 1-4 and the results from FIG. 6. In particular, LED intensity distributions with FWHM values ranging from 3 nm to 20 nm were generated and $ABS_{Sample-LED}$ calculated. The decrease of absorbance when measuring DNA at 260 nm wavelength as a function of LED FWHM was found to be less significant than the decrease of BSA absorbance at 280 nm. Allowing for a 5% decrease in absorbance, the FWHM of the detection system could be increased from 2.5 nm (spectral bandwidth of the spectrophotometer) to 9 nm and 13 nm for BSA at 280 nm and DNA at 260 nm, respectively.

Relative spectral intensity distributions of UV LEDs with a center wavelength at 260 nm and 280 nm as a function of wavelength were measured with a spectrophotometer. The resolution of the spectrometer was confirmed to be 2.5 nm using a mercury spectral calibration lamp at 253.7 nm wavelength. Further, center-wavelength matched interference filter with a resolution of 10 nm were placed between UV-LED and the fiber coupling block to restrict their spectral output (FIG. 6). The center wavelengths of the 260 nm and 280 nm LED were found to be 262 and 281 nm, respectively. FWHM of both LEDs was 13 nm and 10 nm, respectively. Although the FWHM of both LEDs may be adequate, light intensity above 10% can be seen from 262 nm to 278 nm for the 260 nm LED and 281 nm to 293 nm for the 280 nm LED. As light at these wavelengths may interfere with the sample measurement, interference filters were employed. Compared to the raw intensity distribution of the LEDs, the FWHM of the 260 nm/filter combination was reduced to 8 nm and the 280 nm/filter combination to 7 nm wavelength. More importantly, the intensity distributions became symmetric to the center wavelength and the overlapping light levels in the 265 nm to 275 nm region were significantly reduced. These separate optical components can be replaced by coating the front end 82, 84, 86 of the coupling fiber with an interference filter of appropriate wavelength.

Figure 5:
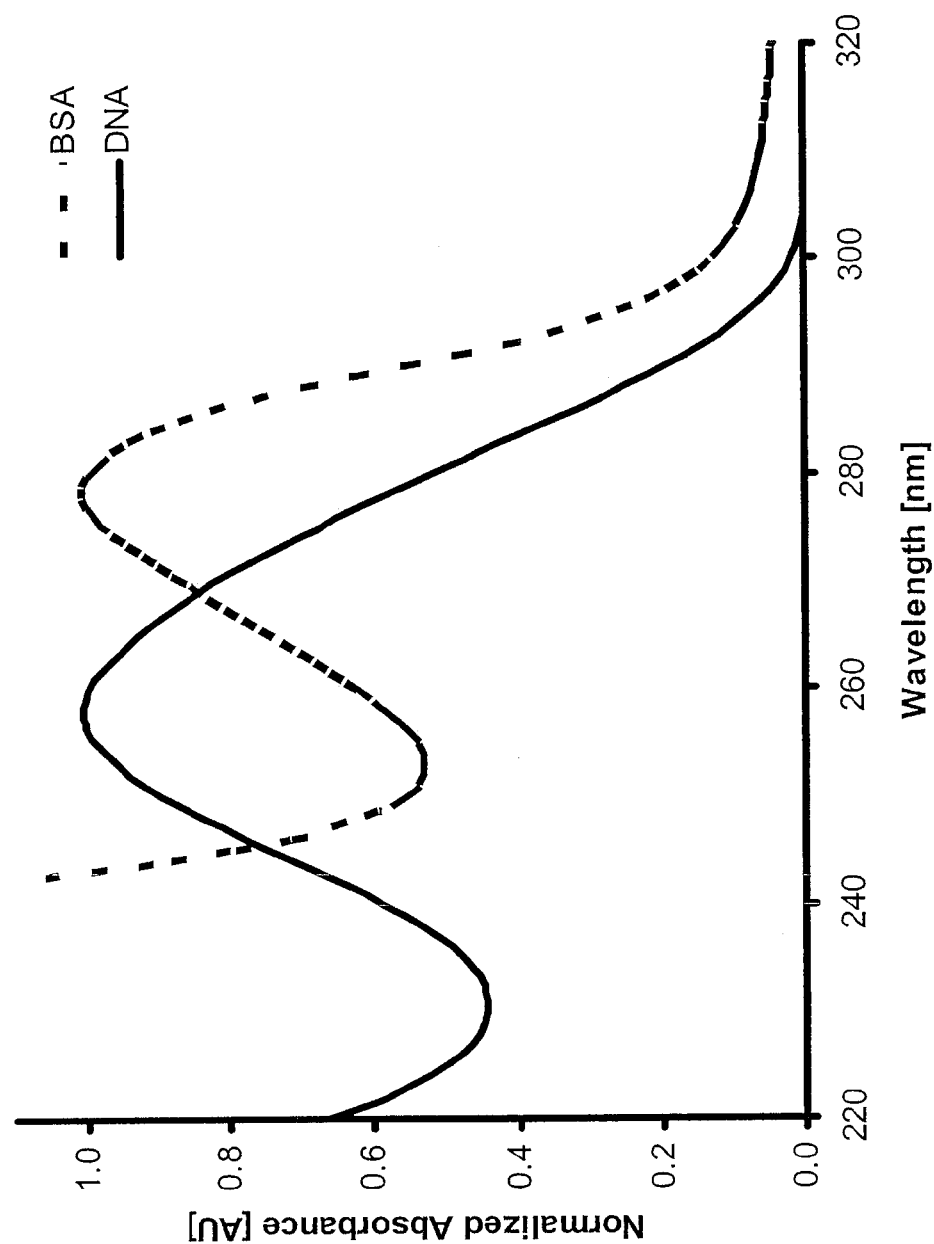
FIG. 5 is a graph of a normalized absorbance for DNA and Protein (BSA)
Figure 8:
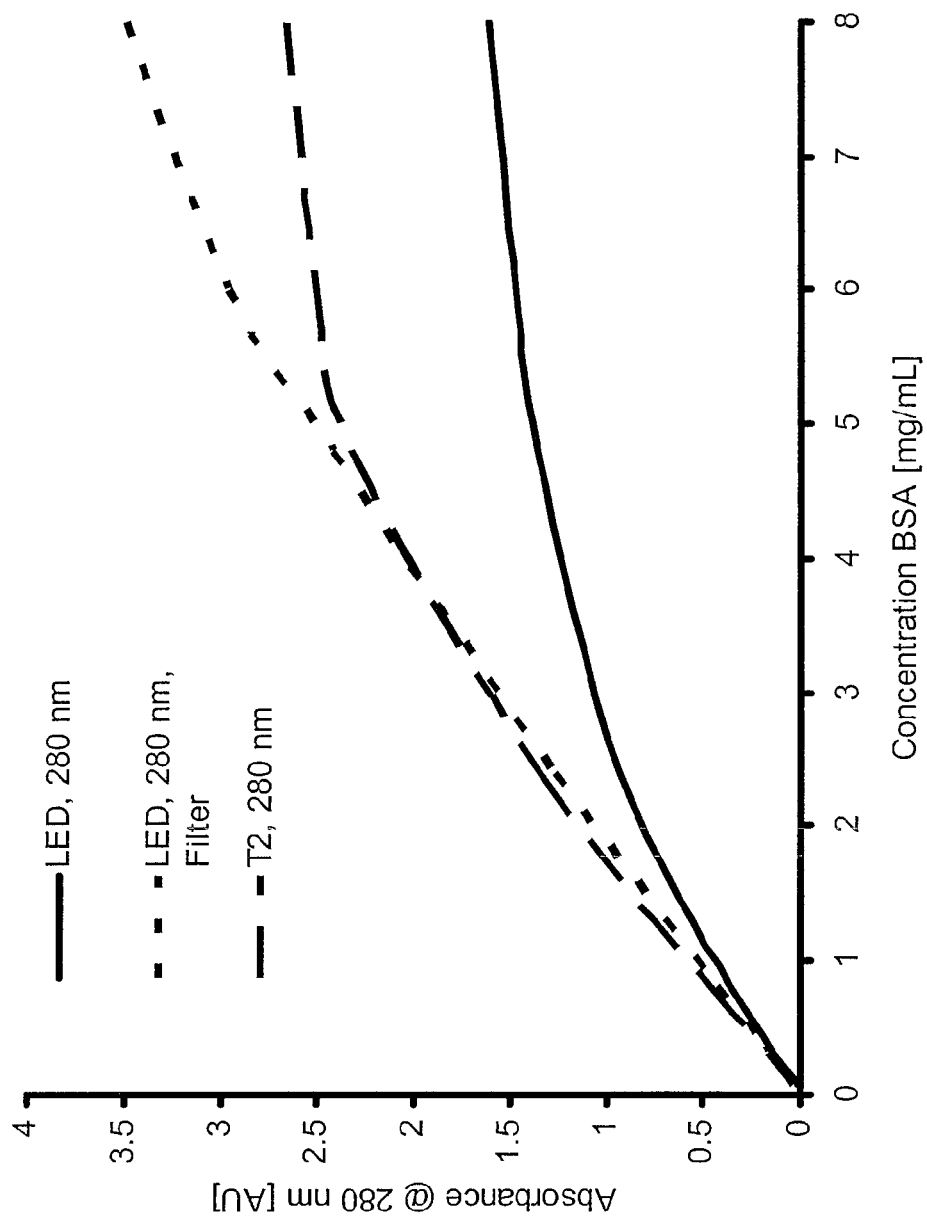
FIG. 8 is a graph of absorbance of BSA at 280 nm versus concentration measured with a TIDAS II™ spectrophotometer and an LED detection system with and without a 10 nm bandpass filter.

BSA concentrations in the region of 0.1 mg/L to 8 mg/L were prepared by gravimetric dilution in ultrapure water. Absorbance was measured at 280 nm with a spectrophotometer and the LED detection system 100 (FIG. 8). For comparison, absorbance was measured with and without the interference filter. The TIDAS II™ spectrophotometer marketed by World Precision Instruments, Inc. exhibits a typical concentration to absorbance calibration. A linear behavior is found between 0 and 2.3 AU; then, the stray light of the detector limits the detection range. The LED detection system 100 without the 280 nm interference filter shows strongly non linear behavior between concentration and absorbance. This can be explained by the fact, that the 280 nm LED emits light up to 310 nm wavelength, where there is only minor absorbance of BSA (FIG. 5). This effect is responsible for the increasing non-linearity of the calibration curve, as the portion of light in this region stays constant and reduces the total absorbance signal observed by the sample photodiode 41 (FIG. 8). However, after the 280 nm bandpass filter is implemented, spectral bandwidth of the 280 nm LED is greatly reduced to 7 nm FWHM (FIG. 8).

With the filter installed, the concentration to absorbance calibration improves significantly. Up to 3.0 AU can be measured with this setup resulting into a $R^2$ of 0.9991 in this range. The spectrophotometer used for comparison only allows for an upper detection limit of 2.3 AU due to stray light effects within its polychromator. The greater dynamic range of the LED detection system can be explained by the monochromatic nature of the detection system. Only light at the wavelength of interest is generated with the LED detection system and used for the measurement.

The LED detection system 200 which employs seven LEDs 51-57 is adapted for use in oceanographic and process applications. The selected wavelengths are indicated. Band pass or short pass filters 91-97 reduce the spectral bandwidths of the emitted radiation.

The invention claimed is:

1. A method for spectroscopically analyzing a sample in a cell comprising:
    (a) sequentially energizing a plurality of LEDs of different selectable wavelengths;
    (b) directly coupling each of said plurality of LEDs to an optical fiber;
    (c) forming said optical fibers into a single bundle;
    (d) coupling said bundle to a large core fiber acting as a multimode mixing element and having an output;
    (e) generating a generally even power distribution at the mixing element output;
    (f) simultaneously coupling light from said mixing element output to a reference detector and to a plurality of sample fiber optic output ports via a secondary fiber optic bundle;
    (g) coupling light from said output ports to the input of a sample cell via a third plurality of optical fibers;
    (h) coupling light from the output of the sample to individual detector elements via a fourth plurality of optical fibers;
    (i) analyzing the spectroscopic change of each sample placed in the individual sample cell simultaneously by the detector elements for each wavelength;
    (j) correcting LED drift or noise by comparison with said reference detector; and
    (k) performing multiple wavelength analyses with the sequentially energized LEDs.

2. The method of claim 1 further comprising filtering said radiation of step (a) to reduce the bandwidth.

3. The method of claim 2 wherein the step of filtering comprises positioning a bandpath filter element between each LED and the coupling fiber of step (b).

4. The method of claim 3 wherein the coupling fiber comprises a front face and said filter element comprises a coating applied to said front face.

5. The method of claim 1 wherein filtering said radiation comprises coating a face of at least one of said optical fibers.

6. The method of claim 1 wherein step (a) further comprises emitting a train of pulses with a selected wavelength.

7. The method of claim 6 wherein the step of pulsing the LEDs comprises producing a sequence of intervals of no emitted radiation and further comprising comparing radiation detected at said reference detector during emission to radiation detected during a no emission interval to compensate for stray radiation.

8. The method of claim 1 wherein the step of correcting further comprises generating a signal indicative thereof and using the signal to determine the presence of the sample.

9. The method of claim 1 wherein the sample cell is a liquid wavelength capillary cell.

10. The method of claim 1 comprising making a measurement of light background when said LEDs are not excited and comparing the measurement to a measurement of a sample.

11. A method for spectroscopically analyzing a sample in a cell comprising:
    (a) sequentially energizing a plurality of LEDs wherein each LED emits radiation at a selected wavelength;
    (b) mixing the radiation emitted from each LED to form mixed radiation;
    (c) transmitting the mixed radiation to the cell and optically coupling the mixed radiation to the sample via a first fiber optic element;
    (d) transmitting the radiation from the sample via a second fiber optic element to a sample photodetector;
    (e) transmitting the radiation from each LED via a third fiber optic element to a reference photodetector; and
    (f) comparing the radiation simultaneously detected by said sample photodetector and said reference photodetector.

12. The method of claim 11 wherein step (a) further comprises pulsing said LEDs.

13. The method of claim 11 further comprising filtering said radiation of step (a) to reduce the bandwidth.

14. The method of claim 13 wherein filtering said radiation comprises coating at least one of said fiber optic elements.

15. The method of claim 11 wherein the step of comparing comprises generating a signal indicative thereof and further comprising using the signal to determine the presence of the sample.

16. The method of claim 11 wherein the cell is a liquid wavelength capillary cell.

17. An instrument for spectroscopically analyzing a sample comprising:
    a first LED which emits radiation at a first wavelength;
    a second LED which emits radiation at a second wavelength;
    a mixer which mixes radiation at said first and second wavelengths to form mixed radiation;
    a first transmitter channel comprising a fiber optic element to transmit radiation from the first LED to a first optical output port;
    a second transmitter channel comprising a fiber optic element to transmit radiation from the second LED to a second optical output port;
    a reference photodetector;
    a first reference channel comprising a fiber optic element to transmit radiation from the first LED to the reference photodetector;
    a second reference channel comprising a fiber optic element to transmit radiation from the second LED to the reference photodetector;
    a first sample photodetector in optical communication with a first input optical port;
    a second sample photodetector in optical communication with a second input optical port; and a microcontroller in simultaneous communication with said first LED and second LED and said reference, first sample and second sample photodetectors so that said LEDs are energized and first and second signals indicative of radiation detected by said first and second sample photodetectors and a reference signal indicative of radiation detected by said reference photodetector are generated.

18. The instrument of claim 17 further comprising a filter which filters radiation to at least one transmitter channel.

19. The instrument of claim 17 further comprising a driver for each LED, said driver being responsive to signals generated by said microcontroller.

20. The instrument of claim 17 further comprising a converter in communication with said photodetectors and said microcontroller, wherein the intensities of the radiation emitted by the LEDs are scaled.

* * * * *